United States Patent [19]

Krafft

[11] Patent Number: 5,679,289
[45] Date of Patent: Oct. 21, 1997

[54] METHOD FOR THE SYNTHESIS AND USE OF PENTAFLUOROPHENYL LITHIUM TO PRODUCE TETRAKIS PENTAFLUOROPHENYL BORATE

[75] Inventor: Terry E. Krafft, Longmont, Colo.

[73] Assignee: Boulder Scientific Company, Mead, Colo.

[21] Appl. No.: 734,954

[22] Filed: Oct. 23, 1996

[51] Int. Cl.$^6$ .................................. C07F 1/02; C07F 5/02
[52] U.S. Cl. ........................... 260/665 R; 568/1; 558/298
[58] Field of Search ..................... 260/665 R; 568/1; 558/258

[56] References Cited

U.S. PATENT DOCUMENTS 5,362,423  11/1994  Ikeda et al. ..................... 260/665 R
5,496,960  3/1996   Piers et al. ..................... 568/1 X
5,600,004  2/1997   Diefenbach ...................... 568/1
5,626,798  5/1997   Schwindemann et al. .......... 260/665 R

*Primary Examiner*—Paul F. Shaver
*Attorney, Agent, or Firm*—Edward S. Irons

[57] ABSTRACT

Procedures are disclosed which preclude significant safety hazards in the production of bulk quantities pentafluorophenyl lithium. A pentafluorophenyl compound is reacted with an alkyl lithium compound in a reaction zone, preferably temperature controlled, under conditions such that only a small amount of a predetermined quantity of pentafluorophenyl lithium product is present in the reaction zone at any time. The product may be directly discharged from the reaction zone for combination with another reactant.

14 Claims, No Drawings

METHOD FOR THE SYNTHESIS AND USE OF PENTAFLUOROPHENYL LITHIUM TO PRODUCE TETRAKIS PENTAFLUOROPHENYL BORATE

TECHNICAL FIELD

This invention relates to methods for the synthesis of pentafluorophenyl lithium and to the production of chemicals derived from pentafluorophenyl lithium. More particularly, the invention relates to methods which reduce the safety hazards which may be associated with the bulk preparation of pentafluorophenyl lithium and its use to synthesize other chemicals.

BACKGROUND OF THE INVENTION

Tetrakis (pentafluorophenyl) borate derivatives are extensively used as olefin polymerization co-catalysts with cyclopentadienyl transition metal complexes. See, e.g., U.S. Pat. No. 5,470,993, column 17, line 20 to column 18, line 10 (listing certain trisubstituted amonium salts of tetrakis (pentafluorophenyl) borates useful as activating co-catalysts). Pentafluorophenyl lithium is frequently used as the source of the pentafluorophenyl group. The synthesis of such borate derivatives is constrained by the tendency of pentafluorophenyl lithium to decompose as the temperature increases. Explosive decomposition has been reported. Hence, pentafluorophenyl lithium is usually generated and used at low temperatures such as −78° C. See generally published European patent application 0604961 A2, Col. 1, ll. 23–28.

SUMMARY OF THE INVENTION

Pursuant to this invention, a pentafluorophenyl compound and an alkyl lithium compound are combined in a reaction zone under conditions such that only a small percentage of a predetermined amount of pentafluorophenyl lithium product is present in the reaction zone at any time. Preferably, the reaction zone is temperature controlled and the pentafluorophenyl lithium reaction product is discharged directly from the reaction zone, without isolation or purification, for combination with another compound, for example, a reactant or reactants effective to produce a tetrakis (pentafluorophenyl) borate.

DEFINITIONS

Pentafluorophenyl compound or reactant

A compound having the formula $C_6F_5X$ in which X is hydrogen, chlorine, bromine or iodine.

Alkyl Lithium

A compound having the formula RLi in which R is a straight or branched chain saturated or unsaturated alkyl group having 1 to 8 carbon atoms. R is preferably a normal or branched chain 1 to 6 carbon atom alkyl group. Normal and butyl lithium are preferred. Alkyl lithium compounds are preferably utilized in 1 to 10 molar solution in a non-interfering hydrocarbon solvent, preferably a 5 to 10 carbon atom aliphatic hydrocarbon solvent such as hexane. n-butyl lithium is commercially available in solution in hexanes.

Predetermined amount of pentafluorophenyl lithium

The total amount of pentafluorophenyl which it is desired to produce at particular times or for reaction with a particular quantity of another reaction. The expression contemplates the standard practice of selecting reactants in amounts needed to provide a given amount of an expected reaction product under the conditions utilized. For example, a stoichiometric amount or more or less than a stoichiometric amount may be selected a priori to produce the consequent predetermined amount of the desired reaction product.

Small percentage of predetermined amount

A percentage which, under the conditions, presents a significantly reduced safety hazard, e.g., less than 50%, preferably less than 25% of the predetermined amount of lithium pentafluorobenzene. Such small percentage is established and maintained, for example, by continuous mixing or agitation of the pentafluorophenyl and alkyl lithium reactants in and prompt discharge of the reaction mixture from the reaction zone.

Non-interfering Solvent

A solvent or mixture of solvents which does not adversely affect the pentafluorophenyl or the alkyl lithium reactants, the pentafluorophenyl lithium synthesis or the reaction of pentafluorophenyl lithium with a subsequent reactant.

Subsequent Reactant

A compound which reacts, preferably directly, with pentafluorophenyl lithium as produced, for example, in the temperature controlled mixing/feed tube of FIG. 1 or in the reaction vessel 12 of FIG. 2 to produce a useful product. Such subsequent reactants include but are not limited to $(C_6F_5)_3B$, compounds having the formula $BX_3$ in which X is a halide, e.g., $BF_3$ or $BCl_3$, or X is an anionic group such as $OR^{31}$ or $NR_2^{31}$, in which R is a straight or branched chain 1 to 10 carbon atom alkyl or aryl group or MZn in which M is a metal, or metalloid, preferably nickel, Z is a halide, preferably chlorine or an anionic group such as $OR^{31}$ and $NR_2^-$, in which R is as defined above, and n indicates the number of Z entities required to satisfy the formal valance of M. Such compounds include $NiCl_2$ and $NiBr_2$.

Controlled Temperature

A reaction zone in which the temperature is controlled to preclude explosive decomposition of pentafluorophenyl lithium under the extant conditions. A person skilled in the art may determine such temperature in known manner. The temperature is preferably controlled not to exceed 50° C. and is preferably maintained in the range of 0° C. to −30° C.

DETAILED DESCRIPTION OF THE INVENTION

Pursuant to the invention a desired amount of pentafluorophenyl lithium is pre-determined. A reaction zone, preferably temperature controlled, is provided. Quantities of a pentafluorophenyl reactant in solution in a non-interfering solvent and of an alkyl lithium reactant in solution in a non-interfering solvent are provided in separate vessels. These reactant solutions are combined with substantially continuous agitation, e.g., stirring, in the reaction zone and the resulting reaction mixture is discharged at a rate such that only a small percentage, i.e., less than 50%, preferably less than 25% of said predetermined amount of pentafluorophenyl lithium is present in said reaction zone at any time.

One embodiment of the invention is described by reference to FIG. 1 in which a solution of bromopentafluorobenzene (BPFBZ) reactant in a non-interfering ethyl ether solvent in container 1 may be passed through line 2 to metering pump 3 through line 4 into temperature controlled mixing line 5. n-butyl lithium reactant in solution in hexane may be passed from container 6 through line 7 and metering pump 8 through line 9 into line 5 for reaction with bromopentafluorobenzene from container 1.

The amounts of these reactants in containers 1 and 6 are appropriate to provide a predetermined amount of pentafluorophenyl lithium product. The metering pumps 3 and 8 are adjusted to preclude the formation in the reaction zone of more than a small percentage of the predetermined amount of pentafluorophenyl lithium.

Pentafluorophenyl lithium produced in line 5 is discharged directly into reaction vessel 10 fitted with stirrer 11 charged with an agitated solution of subsequent reactant, e.g., $(C_6F_5)_3B$, in a non-interfering solvent.

Alternatively, the two solutions in containers 1 and 6 are precooled and mixed without further cooling in line 5.

The reaction mixture in vessel 10 is agitated, preferably stirred, for a time sufficient to permit completion of the reaction.

The embodiment of the invention depicted by FIG. 2 is similar to that shown by FIG. 1 with the exception that the temperature controlled mixing line 5 is replaced by temperature controlled mixing vessel 12 into which the lines 4 and 9 directly discharge the bromopentafluorobenzene and n-butyl lithium reactants. The mixed reactants and the reaction product are discharged continuously from mixing vessel 12 into vessel 13 in which the reaction mixture is agitated by stirrer 14.

EXAMPLE 1

Bromopentafluorobenzene (3.78 g) in ether (50 ml) was reacted with nBuLi (9.38 ml, 1.6M) in hexanes in a controlled temperature mixing zone for less than two minutes. The average temperature in the mixing zone was 12° C. Pentafluorophenyl lithium containing reaction was fed into a solution of subsequent reactant $(C_6F_5)_3B$ (7.68 g in 215 g of a hydrocarbon (Isopar) solvent) (Isopar is a trademark of Exxon Company) in such a way that the residence time in the mixing zone was one minute. Lithium tetrakis (pentafluorophenyl) borate etherate was isolated (12.3 g, 94.1% yield) as the product of the reaction.

EXAMPLE 2

Bromopentafluorobenzene (3.90 g) in ethyl ether (50 mL) was combined with nBuLi (9.41 mL, 1.6M) in hexanes in a controlled temperature mixing zone. The average temperature in the mixing zone was -24° C. The mixture was fed into a solution of $(C_6F_5)_3B$ (7.71 g in 216 g of Isopar solvent) in such a way that the residence time in the mixing zone was one minute and twenty seconds. Lithium tetrakis (pentafluorophenyl) borate etherate was isolated (12.4 g, 94.5%) as the product of the reaction.

EXAMPLE 3

Pentafluorobenzene (2.6 g) in ethyl ether (50 mL) was combined with nBuLi (9.71 mL, 1.6M) in hexanes in a controlled temperature mixing zone. The mixture was fed into a solution of subsequent reactant $(C_6F_5)_3B$ (7.96 g in 223 g of Isopar solvent) in such a way that the residence time in the mixing zone was one minute and fifteen seconds. The average temperature in the mixing zone was -2.4° C. Lithium tetrakis (pentafluorophenyl) borate etherate was isolated (12.6 g, 93.1% yield) as the product of the reaction.

Another aspect of the invention includes, as a first step, the preparation of a mixture of a subsequent reactant, e.g., $(C_6F_5)_3B$, and a pentafluorophenyl compound, precooling the mixture to a temperature of, for example, -10° C. to -40° C. and adding n-butyl lithium in a non-interfering solvent to the mixture which is allowed to warm to room temperature. In one embodiment of this aspect of the invention, an ether, e.g., ethyl ether, may be added to the pre-cooled mixture of pentafluorophenyl compound and $(C_6F_5)_3B$. This procedure is illustrated by the following Example 4.

EXAMPLE 4

Bromopentafluorobenzene (3.90 g) was combined with $(C_6F_5)_3B$ (7.92 g in 222 g of Isopar). Ether (50 ml) was added and the mixture was cooled to -32° C. nBuLi (9.67 mL, 1.6M) in hexanes was added and the mixture was allowed to warm to room temperature. Lithium tetrakis (pentafluorophenyl) borate etherate was isolated (10.1 g, 74.9% yield) as the product of the reaction. $^{19}F$ NMR indicated a purity of 88.3% and $^1H$ NMR showed no butyl groups contained in the product.

I claim:

1. A method for producing a pentafluorophenyl lithium product which comprises
   (i) predetermining an amount of pentafluorophenyl lithium to be produced;
   (ii) providing a first vessel containing a solution of a pentafluorophenyl compound in a first non-interfering solvent;
   (iii) providing a second vessel containing a solution of an alkyl lithium in a second non-interfering solvent which may be the same as or different from said first non-interfering solvent;
   (iv) separately causing the contents of said first vessel and of said second vessel to be discharged at controlled rates into a reaction zone to produce a first reaction mixture containing pentafluorophenyl lithium in solution in said non-interfering solvents;
   said rates of discharge being controlled to preclude the formation at any time in said reaction of more than a minor percentage of said predetermined amount of said pentafluorophenyl lithium product.

2. The claim 1 method in which said minor percentage of said pentafluorophenyl lithium product is less than 25% of said predetermined amount of said pentafluorophenyl lithium.

3. A method for producing a pentafluorophenyl lithium product which comprises
   (i) predetermining an amount of pentafluorophenyl lithium to be produced;
   (ii) providing a first vessel containing a solution of a pentafluorophenyl compound in a first non-interfering solvent;
   (iii) providing a second vessel containing a solution of an alkyl lithium in a second non-interfering solvent which may be the same as or different from said first non-interfering solvent;
   (iv) separately causing the contents of said first vessel and of said second vessel to be discharged at controlled rates into a reaction zone to produce a first reaction mixture containing pentafluorophenyl lithium in solution in said non-interfering solvents;
   (v) discharging said first reaction mixture directly from said mixing zone into a third vessel containing a subsequent reactant
   wherein said rates of discharge of the contents of said first vessel and said second vessel into said reaction zone and of the discharge of said first reaction mixture into said third vessel are controlled to preclude the formation at any time of more than a minor percentage of said predetermined amount of said pentafluorophenyl lithium product.

4. The claim 1 or claim 3 method in which said reaction zone is a single line from which said first reaction mixture is discharged directly into a vessel containing said subsequent reactant.

5. The claim 1 or claim 3 method in which said reaction zone is a vessel into which a line from said first vessel and a line from said second vessel separately discharge a solution of pentafluorophenyl compound and a solution of an alkyl lithium and from which said first reaction mixture is discharged at a rate which maintains the volume of the contents of said mixing zone vessel substantially constant.

6. The claim 1, 2 or 3 method in which said pentafluorophenyl compound is pentafluorophenyl bromide, pentafluorophenyl chloride or pentafluorobenzene.

7. The claim 1, 2 or 3 method in which said subsequent reactant is $(C_6H_5)_3B$, $BF_3$ or $BCl_3$ $B(OR)_3$ or $B(NR_2)_3$.

8. The claim 1, 2 or 3 method in which the temperature of the contents of said mixing zone is controlled not to exceed 50° C.

9. A method wherein pentafluorophenyl lithium is reacted with a subsequent reactant to produce a third compound comprising a pentafluorophenyl group, the improvement of which comprises:

directly combining the first reaction mixture produced by the claim 1 or claim 3 method with a subsequent reactant to produce a reaction product compound comprising a pentafluorophenyl group.

10. The claim 9 method in which said pentafluorophenyl compound is pentafluorophenyl bromide, pentafluorophenyl chloride or pentafluorobenzene.

11. The claim 9 or claim 10 method wherein said subsequent reactant is $(C_6H_5)_3B$, $BF_3$ or $BCl_3$ $B(OR)_3$ or $B(NR_2)_3$.

12. A method for producing a lithium tetrakis (pentafluorophenyl) borate which comprises:

(i) providing a first vessel containing a solution of a pentafluorophenyl compound in a non-interfering solvent;

(ii) providing a second vessel containing a solution of n-butyl lithium in a non-interfering solvent;

(iii) separately metering the contents of said first vessel and of said second vessel into a mixing zone with continuous agitation for a time period to produce a first reaction mixture containing pentafluorophenyl lithium in solution in said non-interfering solvents;

(iv) discharging said step (ii) reaction mixture directly into a solution of $(C_6F_5)_3B$, $BF_3$, $BCl_3$, $B(OR)_3$ or $B(NR_2)_3$ in a non-interfering solvent to produce lithium tetrakis (pentafluorophenyl) borate, and (v) isolating said lithium tetrakis (pentafluorophenyl) borate etherate.

13. A method for producing a lithium tetrakis (pentafluorophenyl) borate which comprises:

(i) preparing a mixture of a pentafluorophenyl compound and a subsequent reactant in solution in a non-interfering solvent and cooling the resulting mixture to a low temperature;

(ii) adding a solution of an alkyl lithium in a non-interfering solvent and (iii) permitting the resultant reaction mixture to warm to room temperature;

wherein lithium tetrakis (pentafluorophenyl) borate is produced.

14. The claim 13 method in which an ether is added to said solution produced in step (i).

* * * * *